United States Patent
Sudin et al.

(10) Patent No.: US 11,090,464 B2
(45) Date of Patent: Aug. 17, 2021

(54) ROTATIONALLY TORQUABLE ENDOVASCULAR DEVICE WITH ACTUATABLE WORKING END

(71) Applicant: RAPID MEDICAL LTD., Yokneam (IL)

(72) Inventors: Yuri Sudin, Modin (IL); Ronen Eckhouse, Shimshit (IL); Aharon Friedman, Haifa (IL); Matan Gedulter, Givat Ela (IL); Moshe Miller, Jerusalem (IL)

(73) Assignee: Rapid Medical Ltd., Yokneam (IL)

( * ) Notice: Subject to any disclaimer, the term of this patent is extended or adjusted under 35 U.S.C. 154(b) by 0 days.

(21) Appl. No.: 16/388,056

(22) Filed: Apr. 18, 2019

(65) Prior Publication Data
US 2019/0240457 A1 Aug. 8, 2019

Related U.S. Application Data

(63) Continuation-in-part of application No. PCT/IB2017/001663, filed on Sep. 28, 2017.

(60) Provisional application No. 62/401,387, filed on Sep. 29, 2016.

(51) Int. Cl.
| | | |
|---|---|---|
| *A61M 25/01* | (2006.01) | |
| *A61M 25/09* | (2006.01) | |
| *A61B 17/00* | (2006.01) | |

(52) U.S. Cl.
CPC ... *A61M 25/0147* (2013.01); *A61B 17/00234* (2013.01); *A61M 25/09025* (2013.01);
(Continued)

(58) Field of Classification Search
CPC ........ A61M 25/0147; A61M 25/09025; A61M 25/09041; A61M 2025/09066;
(Continued)

(56) References Cited

U.S. PATENT DOCUMENTS

| | | |
|---|---|---|
| 4,815,478 A | 3/1989 | Buchbinder et al. |
| 5,318,529 A | 6/1994 | Kontos |

(Continued)

FOREIGN PATENT DOCUMENTS

WO   WO 2018/060776 A2   4/2018

OTHER PUBLICATIONS

International Search Report and Written Opinion of the International Searching Authority dated Jul. 10, 2018, in International Application No. PCT/IB2017/001663 (10 pages).

(Continued)

*Primary Examiner* — Patrick Fernandes
(74) *Attorney, Agent, or Firm* — Finnegan, Henderson, Farabow, Garrett & Dunner, LLP

(57) ABSTRACT

In one exemplary embodiment, an endovascular device may include a hollow shaft having a proximal end and a distal end, and sized for insertion into a blood vessel. The endovascular device may also include a control line having a proximal end and a distal end, and extending through the hollow shaft. The endovascular device may also include an actuatable working element located proximate the distal end of the hollow shaft, and configured to receive an actuation force transmitted via the distal end of the control line. The endovascular device may further include an actuator configured to exert the actuation force on the proximal end of the control line, to thereby cause relative movement between the control line and the hollow shaft and to actuate the working element. The hollow shaft may also include a cable formed of a plurality of wound wires and including a proximal segment, at least one transition segment, and a distal segment. The proximal segment, at least one transition segment, and distal segment may include different numbers of wires.

9 Claims, 9 Drawing Sheets

(52) U.S. Cl.
CPC . *A61M 25/09041* (2013.01); *A61B 2017/003* (2013.01); *A61B 2017/00323* (2013.01); *A61M 2025/09066* (2013.01)

(58) Field of Classification Search
CPC .... A61B 17/00234; A61B 2017/00323; A61B 7/12113; A61N 2017/003; A61F 2/95
See application file for complete search history.

(56) References Cited

U.S. PATENT DOCUMENTS

| | | | |
|---|---|---|---|
| 5,484,409 | A | 1/1996 | Atkinson et al. |
| 6,566,994 | B1 * | 5/2003 | Jensen ................. G01R 15/181 336/174 |
| 2001/0044633 | A1 | 11/2001 | Klint |
| 2004/0073141 | A1 | 4/2004 | Hartley et al. |
| 2004/0082879 | A1 * | 4/2004 | Klint ........................ A61F 2/95 600/585 |
| 2009/0297582 | A1 * | 12/2009 | Meyer .............. A61B 17/12113 424/423 |
| 2010/0249773 | A1 | 9/2010 | Clark et al. |
| 2014/0207115 | A1 | 7/2014 | Brustad et al. |

OTHER PUBLICATIONS

International Search Report and Written Opinion of the International Searching Authority dated Aug. 6, 2020 in International Application No. PCT/IB2020/000286 (12 pages).

* cited by examiner

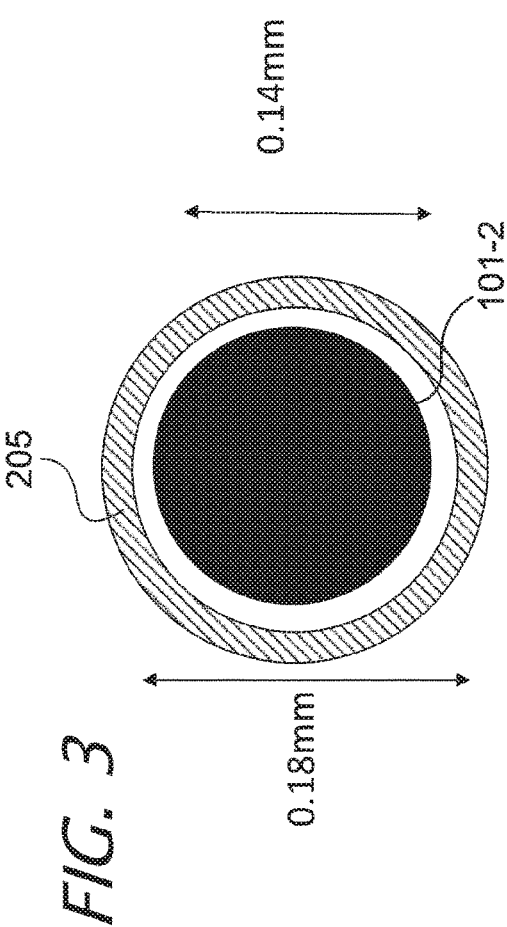
FIG. 3
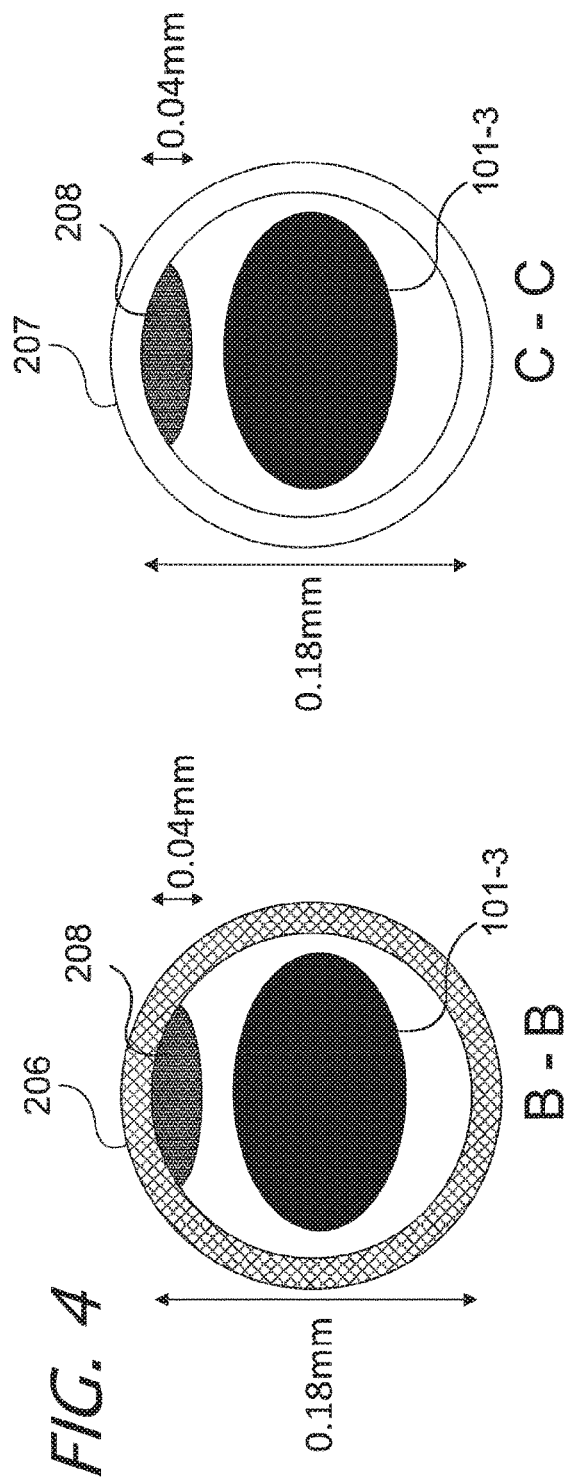
FIG. 5
FIG. 4

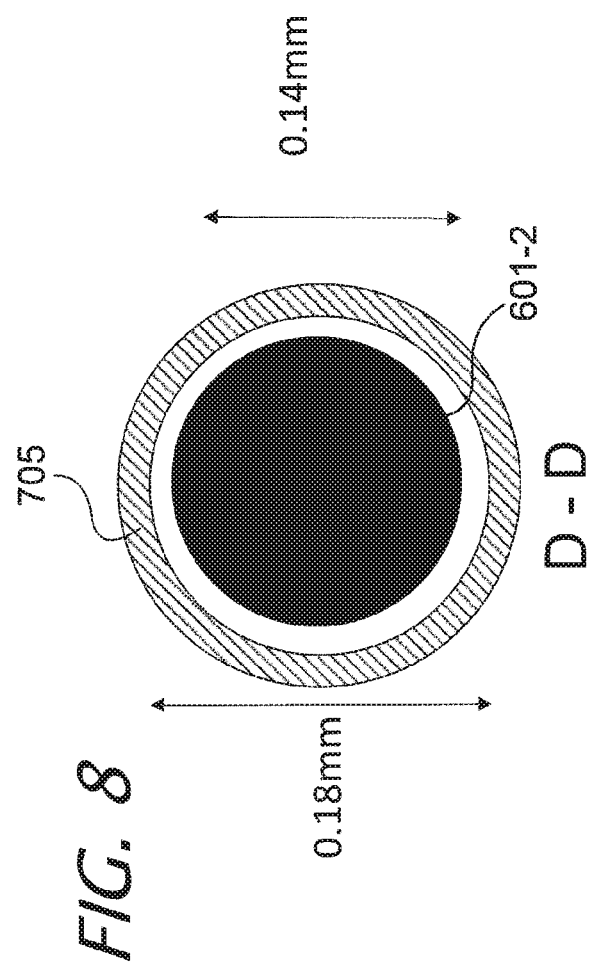
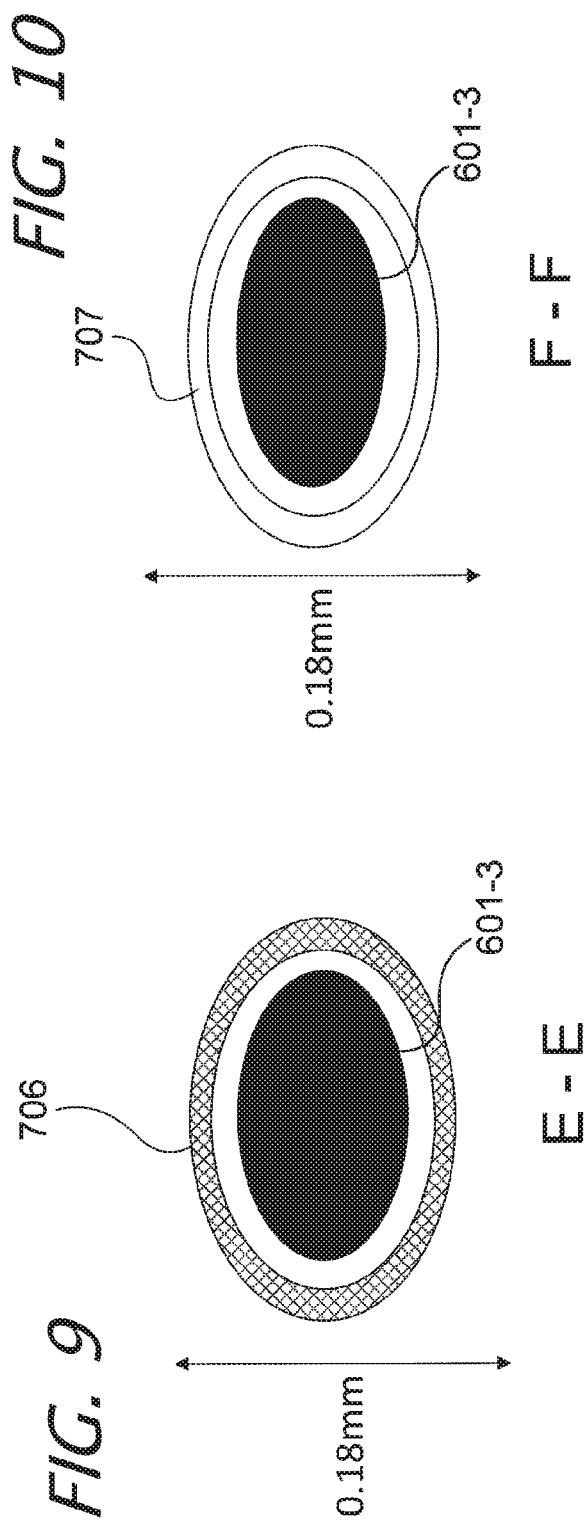

ROTATIONALLY TORQUABLE ENDOVASCULAR DEVICE WITH ACTUATABLE WORKING END

CROSS-REFERENCE TO RELATED APPLICATIONS

This application is a continuation-in-part of PCT Application No. PCT/IB2017/001663, filed Sep. 28, 2017, which claims the benefit of priority from U.S. Provisional Application No. 62/401,387 filed Sep. 29, 2016, both of which are herein incorporated by reference in their entireties.

TECHNICAL FIELD

This disclosure relates generally to endovascular devices. In particular, the disclosure relates generally to endovascular devices comprising a cable formed by a plurality of wound wires to transfer torque while maintaining flexibility and structural strength.

SUMMARY

Embodiments of the present disclosure may include an endovascular device including a hollow shaft having a proximal end and a distal end, a control line having a proximal end and a distal end, an actuatable working element located proximate the distal end of the hollow shaft, and an actuator. The hollow shaft may be sized for insertion into a blood vessel. The control line may extend through the hollow shaft. The actuatable working element may be configured to receive an actuation force transmitted via the distal end of the control line. The actuator may be configured to exert the actuation force on the proximal end of the control line, to thereby cause relative movement between the control line and the hollow shaft and to actuate the working element. The hollow shaft may also include a cable formed of a plurality of wound wires. The cable may include a proximal segment, at least one transition segment, and a distal segment. The proximal segment, the at least one transition segment, and the distal segment may include different numbers of wires.

In some embodiments, the proximal segment of the cable may include a first number of wires, the at least one transition segment may include a second number of wires, which may be less than the first number of wires, and the distal segment may include a third number of wires, which may be less than the second number of wires. The first number of wires may be wound at a first pitch angle, the second number of wires may be wound at a second pitch angle, and the third number of wires may be wound at a third pitch angle. The first, second, and third pitch angles may be determined based on at least one of a diameter of the wires, the number of wires, and a diameter of a winding mandrel. In some embodiments, the first pitch angle may be less than the second pitch angle, and the second pitch angle may be less than the third pitch angle.

In some embodiments, at least one of the plurality of wound wires may be configured to extend from the proximal segment to the distal segment of the cable. In other embodiments, the distal segment may have a flexibility greater than a flexibility of the proximal segment. In yet another embodiment, the cable may include at least three transition segments.

In some embodiments, a rotational force exerted on the proximal end of the hollow shaft may cause the rotational force to be applied to the working element. The ratio of the rotational force exerted on the proximal end of the hollow shaft to the rotational force applied to the working element may be approximately 1:1. In other words, the rotational force exerted on the proximal end of the hollow shaft may be approximately equal to the rotational force applied to the working element. In some embodiments, the cable may be configured to transfer rotational torque to the distal end of the working element when the hollow shaft is rotated.

Embodiments of the present disclosure may also include an endovascular device including a hollow shaft having a proximal end and a distal end, a control line having a proximal end and a distal end, an actuatable working element located proximate the distal end of the hollow shaft, and an actuator. The hollow shaft may be sized for insertion into a blood vessel. The control line may extend through the hollow shaft. The actuatable working element may be configured to receive an actuation force transmitted via the distal end of the control line. The actuator may be configured to exert the actuation force on the proximal end of the control line, cause relative movement between the control line and the hollow shaft, and actuate the working element. The hollow shaft may also include a cable formed of a plurality of wound wires. The cable may include a proximal segment formed of a first number of wires, at least one transition segment formed of a second number of wires less than the first number of wires, and a distal segment formed of a third number of wires less than the second number of wires.

In some embodiments, the first number of wires may be wound at a first pitch angle, the second number of wires may be wound at a second pitch angle, and the third number of wires may be wound at a third pitch angle. The first, second, and third pitch angles may be determined based on at least one of a diameter of the wires, the number of wires, and a diameter of a winding mandrel. In some embodiments, the first pitch angle may be less than the second pitch angle, and the second pitch angle may be less than the third pitch angle.

In some embodiments, at least one of the plurality of wound wires may be configured to extend from the proximal segment to the distal segment of the cable. In other embodiments, the distal segment may have a flexibility greater than a flexibility of the proximal segment. In yet another embodiment, the cable may include at least three transition segments. In some embodiments, the cable may be configured to transfer rotational torque to the distal end of the working element when the hollow shaft is rotated.

Embodiments of the present disclosure may also include a method of manufacturing an endovascular device. The method may include forming a hollow shaft sized for insertion into a blood vessel, disposing a control line having a proximal end and a distal end through the hollow shaft, connecting an actuatable working element at the distal end of the hollow shaft, and connecting an actuator at the proximal end of the control line. The hollow shaft may have a proximal end and a distal end. The actuatable working element may be configured to receive an actuation force transmitted via the distal end of the control line. The actuator may be configured to exert the actuation force on the proximal end of the control line, cause relative movement between the control line and the hollow shaft, and actuate the working element. Forming the hollow shaft may also include winding a plurality of wires at a first pitch angle to form a proximal segment of a cable, cutting at least one of the wires forming the proximal segment, winding a first remainder of the wires at a second pitch angle to form a transition segment of the cable, cutting at least one of the first remainder of the wires forming the transition segment, and winding a second remainder of the wires at a third pitch angle to form a distal segment of the cable.

In some embodiments, a diameter of the winding mandrel may be changed after winding the plurality of wires at the first pitch angle and before winding the first remainder of the wires at the second pitch angle, to thereby compensate for a change in pitch angle. In other embodiments, the diameter of the winding mandrel may be changed after winding the first remainder of the wires at the second pitch angle and before winding the second remainder of the wires at the third pitch angle, to thereby compensate for a change in pitch angle.

Embodiments of the present disclosure may also include a method of manufacturing an endovascular device. The method may include forming a hollow shaft sized for insertion into a blood vessel, disposing a control line having a proximal end and a distal end through the hollow shaft, connecting an actuatable working element at the distal end of the hollow shaft, and connecting an actuator at the proximal end of the control line. The hollow shaft may have a proximal end and a distal end. The actuatable working element may be configured to receive an actuation force transmitted via the distal end of the control line. The actuator may be configured to exert the actuation force on the proximal end of the control line, cause relative movement between the control line and the hollow shaft, and actuate the working element. Forming the hollow shaft may also include winding a plurality of wires at a pitch angle to form a proximal segment of a cable, cutting at least one of the wires forming the proximal segment, decreasing a diameter of a winding mandrel, winding a first remainder of the wires at the pitch angle to form a transition segment of the cable, cutting at least one of the first remainder of the wires forming the transition segment, decreasing the diameter of the winding mandrel, and winding a second remainder of the wires at the pitch angle to form a distal segment of the cable.

BRIEF DESCRIPTION OF THE DRAWINGS

The accompanying drawings, which are incorporated in and constitute a part of this specification, illustrate disclosed embodiments and, together with the description, serve to explain the disclosed embodiments.

FIG. 3 is an illustration of an inner cross section of a section of the exemplary endovascular device of FIG. 2, consistent with at least one of the disclosed embodiments;

FIG. 4 is an illustration of an inner cross section of a section of the exemplary endovascular device of FIG. 2, consistent with at least one of the disclosed embodiments;

FIG. 5 is an illustration of an inner cross section of a section of the exemplary endovascular device of FIG. 2, consistent with at least one of the disclosed embodiments;

FIG. 8 is an illustration of an inner cross section of a section of the exemplary endovascular device of FIG. 7, consistent with at least one of the disclosed embodiments;

FIG. 9 is an illustration of an inner cross section of a section of the exemplary endovascular device of FIG. 7, consistent with at least one of the disclosed embodiments; and FIG. 10 is an illustration of an inner cross section of a section of the exemplary endovascular device of FIG. 7, consistent with at least one of the disclosed embodiments.

Annotations appearing in the figures are exemplary only, and are not restrictive of the invention as claimed.

DETAILED DESCRIPTION

Reference will now be made in detail to the present embodiments (exemplary embodiments) of the disclosure, examples of which are illustrated in the accompanying drawings.

Figure 1:
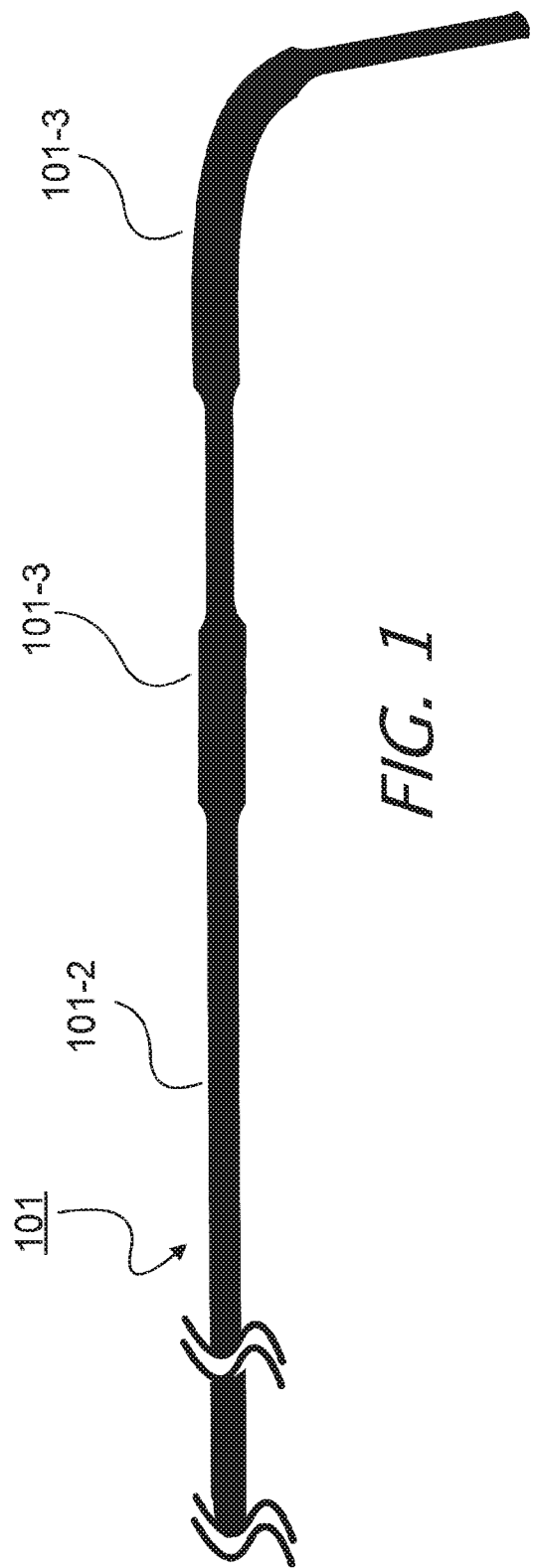
FIG. 1 is an illustration of a control wire for an exemplary endovascular device, consistent with at least one of the disclosed embodiments.
Figure 2:
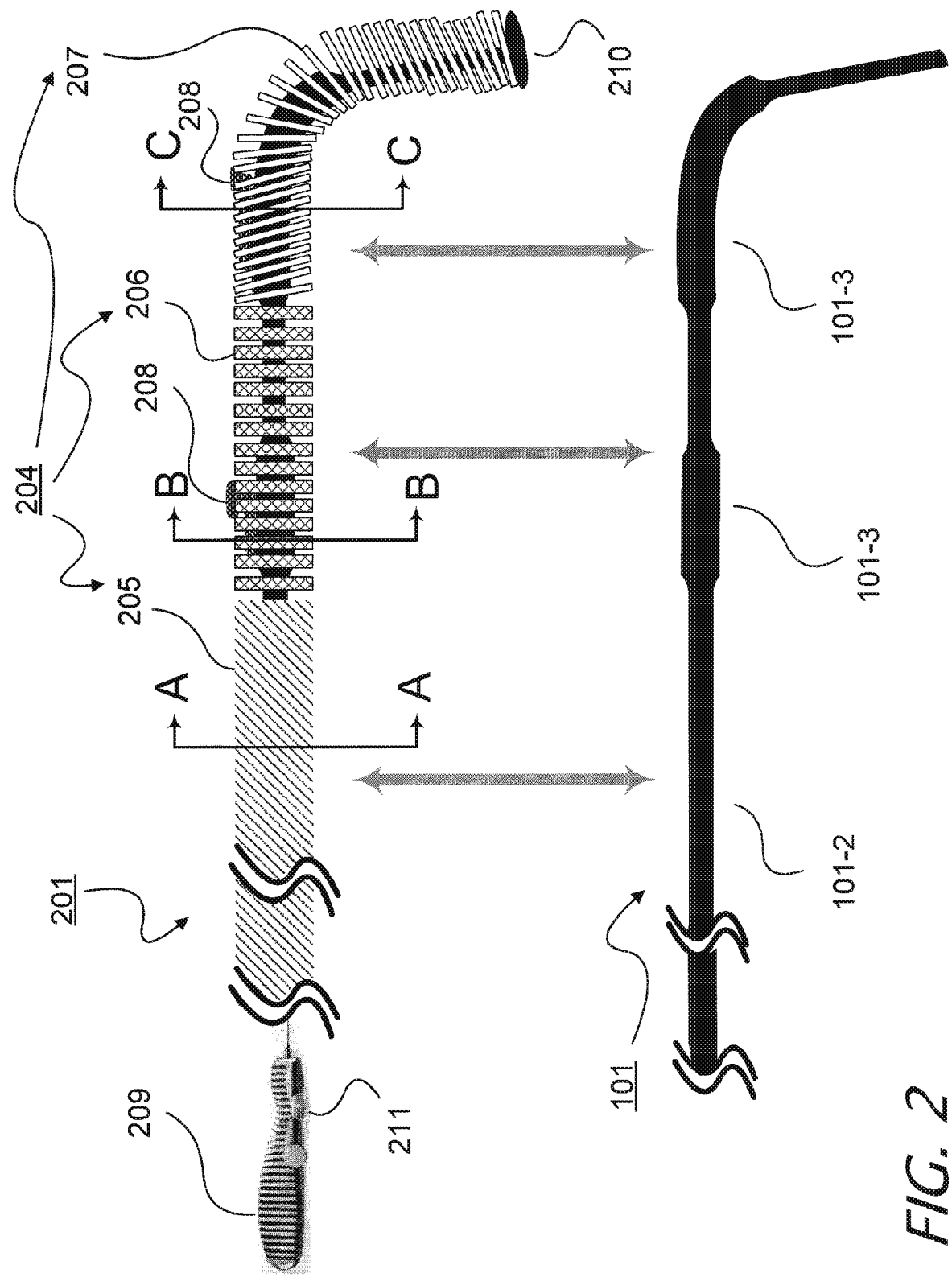
FIG. 2 is an illustration of an exemplary endovascular device with the control wire of FIG. 1, consistent with at least one of the disclosed embodiments.

FIG. 1 illustrates a control wire 101 of an exemplary endovascular device in accordance with the disclosure, which may be deformed or flattened in two zones 101-3, and may be round in other areas along its axis 101-2. FIG. 2 illustrates an exemplary endovascular device 201 using control wire 101 in accordance with the disclosure. (Solely to illustrate the position of zones 101-2 and 101-3 in endovascular device 201, with the understanding that control wire 101 is part of endovascular device 201, FIG. 2 also separately depicts control wire 101 of FIG. 1, with zones 101-3 and 101-2 generally aligned to endovascular device 201.) As shown in FIG. 2, endovascular device 201 may also include an elongated shaft 204 which may include a tube 205, a cable of wires 206, and a single wire coil 207. A distal tip 210 of the elongated shaft 204 may be attached to control wire 101, for example. At a proximal end of the elongated shaft 204, the control wire 101 may be connected to a slider 211 of a handle 209, with the elongated shaft 204 connected to the handle 209 to facilitate the relative movement. (In FIG. 2, handle 209 is not depicted to the same scale as that of elongated shaft 204.) In accordance with at least some embodiments, two polymers 208 may be inserted between the elongated shaft 204 and the control wire 101 to prevent the radial movement between the control wire 101 and the elongated shaft 204.

Consistent with the embodiment shown in FIGS. 9 and 10, in at least some embodiments of an exemplary endovascular device of the disclosure, the cable of wires 206 and the single wire coil 207 of the elongated shaft 204 may be elliptical. This elliptical shape resists relative rotation of the elongated shaft 204 and the control wire 101, enabling torqueing of the device. Alternatively, other non-symmetrical shapes (e.g., cross-sections) may be employed, consistent with the invention to resist rotation and to permit torqueing.

At least some embodiments of an exemplary endovascular device of the disclosure may encompass a fixture enabling transmission of a radial force of the elongated shaft 204 to the control wire 101 with 1:1 ratio. This may be achieved, for example, by preventing axial rotation between the control wire 101 and the elongated shaft 204 without preventing the axial movement between the control wire 101 and the elongated shaft 204. And such axial rotation prevention (without axial movement prevention) may be achieved, for example, by deforming at least a portion of the control wire 101 and making at least a portion of the inner cross section of the round elongated shaft 204 non-round respectively. For example, there may be an overlap between the two rectangular (or flattened) portions 101-3 even during axial movement of the control wire 101 compared to the elongated shaft 204.

A control wire 101 with at least some flat or rectangular section or sections may be achieved by, for example, selectively pressing the control wire 101, by adhesion of additional materials to form a non-round shape, or by other means.

Achieving a non-round inner cross section may be achieved, for example, by attaching rectangular shaped materials 208 to an inner wall of the elongated shaft 204. As another example, a polymer 208 may be inserted through the wire cable to create a non-round cross section. The polymer 208 may be heated and inserted through holes in the wall of the elongated shaft 204 and shaped as needed by a rectangular mandrel.

As shown in FIG. 3, which illustrates an inner cross section A-A of a section of exemplary endovascular device 201, the control wire 101 may be made from 0.14 mm Nitinol wire. A distal tip of the wire 101 may be gradually grinded to an outer diameter of about 70 um. The elongated shaft 204 may be made from a 130 cm Nitinol tube with an inner diameter of 0.18 mm which may be bonded to a PTFE covered cable of ten 70 um Nitinol wires and the distal section may be a single 70 um wire which may be coiled.

As shown in FIG. 4, which illustrates an inner cross section B-B of a section of exemplary endovascular device 201, the control wire 101 may be pressed to create flat sections 101-3 of about 0.16 mm×0.12 mm of 30 mm of length. Using a rectangular mandrel, a polymer 208 may be inserted through the wire cable 206 to create a non-round cross section in areas that overlap the non-round sections of the control wire 101. As a result, relative axial movement between the control wire 101 and the elongated shaft 204 may be maintained while the axial rotation between the control wire 101 and the elongated shaft 204 (which includes cable 206) may be prevented.

FIG. 5 illustrates an inner cross section C-C of a section of exemplary endovascular device 201, similar to cross section B-B of FIG. 4. Again, as a result, relative axial movement between the control wire 101 and the elongated shaft 204 may be maintained while the axial rotation between the control wire 101 and the elongated shaft 204 (which includes single wire coil 207) may be prevented.

Figure 6:
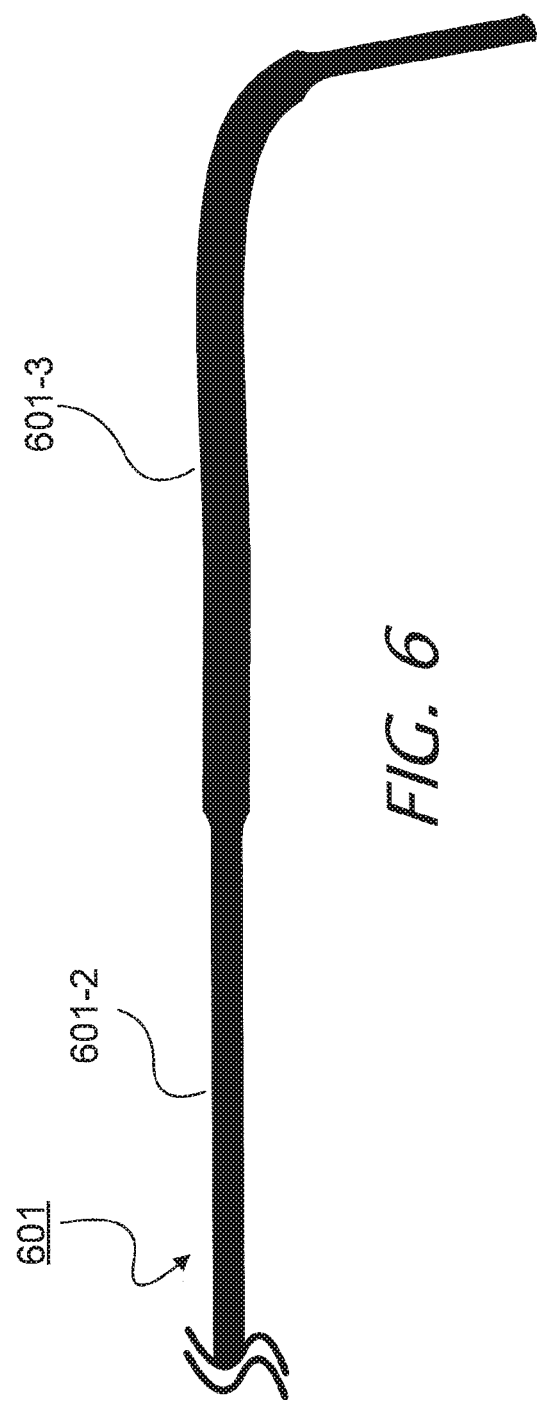
FIG. 6 is an illustration of a control wire for another exemplary endovascular device, consistent with at least one of the disclosed embodiments.
Figure 7:
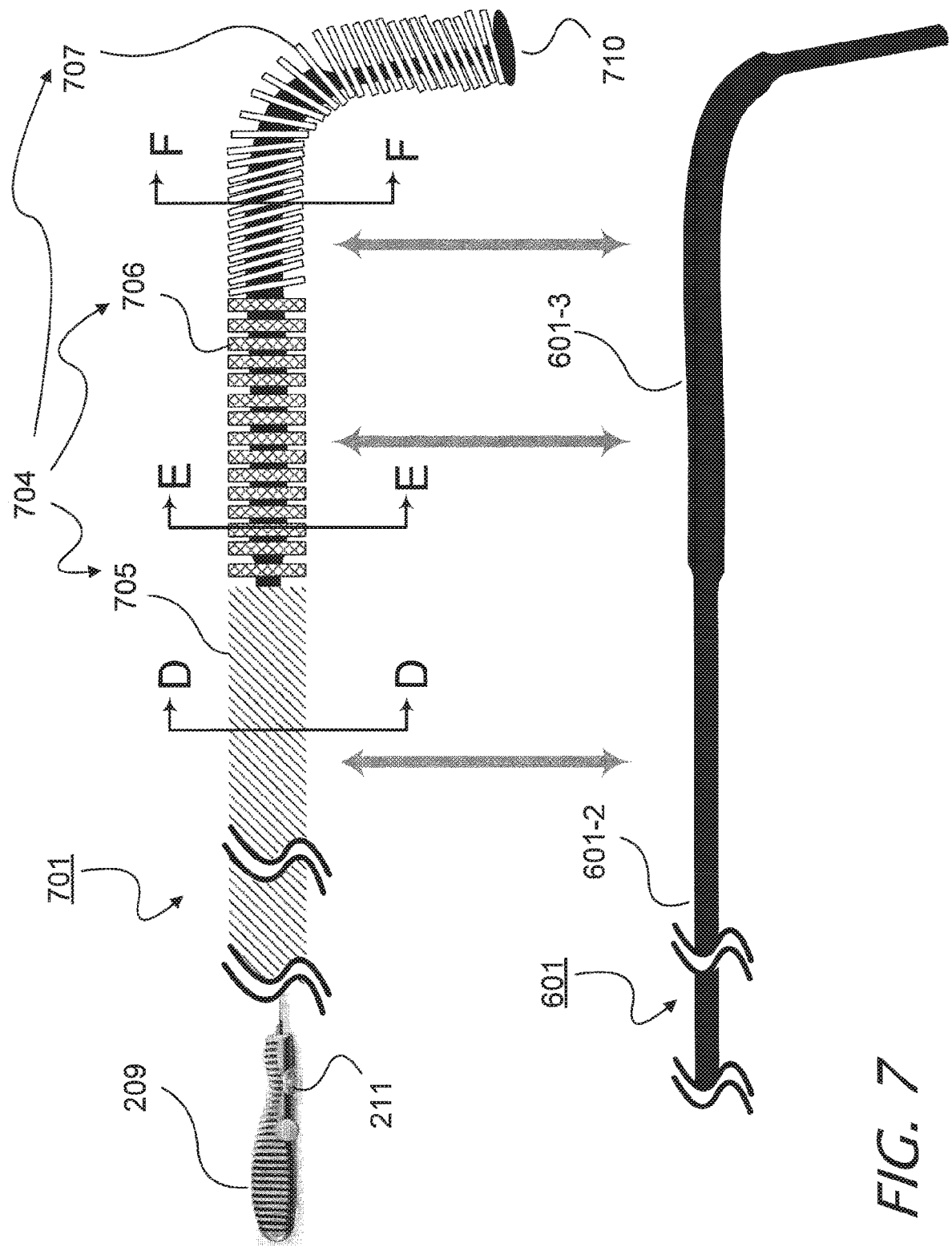
FIG. 7 is an illustration of an exemplary endovascular device with the control wire of FIG. 6, consistent with at least one of the disclosed embodiments.

In a further embodiment, FIG. 6 illustrates a control wire 601 of an exemplary endovascular device in accordance with the disclosure, which may be deformed or flattened in zone 601-3, and may be round in other areas along its axis 601-2. FIG. 7 illustrates an exemplary endovascular device 701 using control wire 601 in accordance with the disclosure. (Solely to illustrate the position of zones 601-2 and 601-3 in endovascular device 701, with the understanding that control wire 601 is part of endovascular device 701, FIG. 7 also separately depicts control wire 601 of FIG. 6, with zones 601-3 and 601-2 generally aligned to endovascular device 701.) As shown in FIG. 7, endovascular device 701 may also include an elongated shaft 704 which may include a tube 705, a cable of wires 706, and a single wire coil 707. A distal tip 710 of the elongated shaft 704 may be attached to control wire 601, for example. At a proximal end of the elongated shaft 704, the control wire 601 may be connected to a slider 211 of a handle 209, with the elongated shaft 704 connected to the handle 209 to facilitate the relative movement. (In FIG. 7, handle 209 is not depicted to the same scale as that of elongated shaft 704.)

FIG. 8 illustrates an inner cross section D-D of a section of exemplary endovascular device 701. The control wire 601 may be made from 0.14 mm Nitinol wire. A distal tip of the wire 601 may be gradually grinded to an outer diameter of about 70 um. The elongated shaft 704 may be made from a 130 cm Nitinol tube with an inner diameter of 0.18 mm which may be bonded to a PTFE covered cable of ten 70 um Nitinol wires and the distal section may be a single 70 um wire which may be coiled.

As shown in FIGS. 9 and 10, which illustrates inner cross sections E-E and F-F of a section of exemplary endovascular device 701, the control wire 601 may be pressed to create flat sections 101-3 of about 0.16 mm×0.12 mm of 30 mm of length. As mentioned above, in FIGS. 9 and 10, the cable of wires 706 and the single wire coil 707 of the elongated shaft 704 may be elliptical. This elliptical shape resists relative rotation of the elongated shaft 704 and the control wire 601, enabling torqueing of the device. Alternatively, other non-symmetrical shapes (e.g., cross-sections) may be employed, consistent with the invention to resist rotation and to permit torqueing.

In other embodiments, a single wire coil may be provided, extending from a multi-wire cable with a control wire that runs through the core of both. This enables the control wire to steer the more flexible coiled end of the coil, without causing the multi-wire cable to appreciably bend.

Figure 11A:
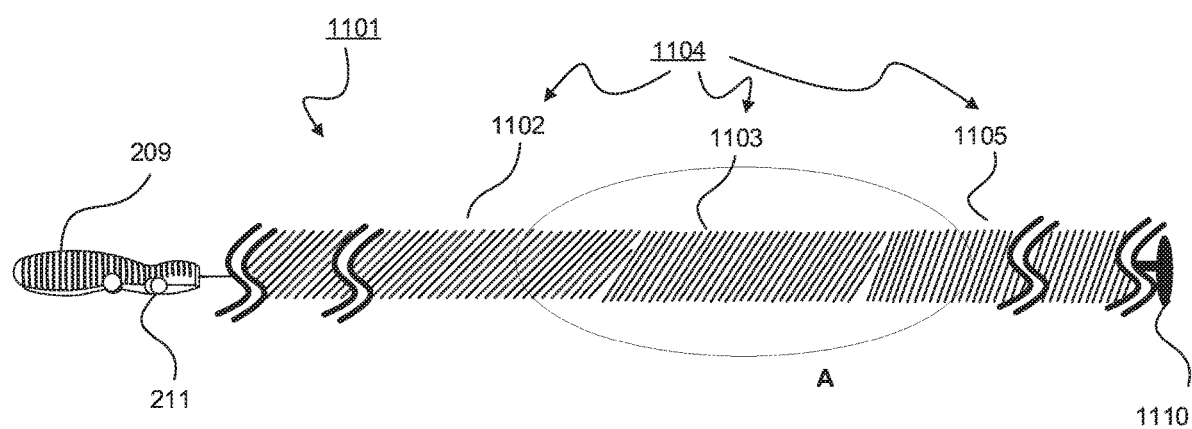
FIG. 11A is an illustration of an exemplary endovascular device, consistent with at least one of the disclosed embodiments.

FIG. 11A illustrates an exemplary endovascular device 1101, according to the disclosure. As shown in FIG. 11A, endovascular device 1101 may also include an elongated shaft 1104, which may include a cable of wires, including a proximal segment 1102, at least one transition segment 1103, and a distal segment 1105. A distal tip 1110 of the elongated shaft 1104 may be attached to control wire 101 (as shown in FIG. 1), for example. At a proximal end of the elongated shaft 1104, the control wire 101 may be connected to a slider 211 of a handle 209, with the elongated shaft 1104 connected to the handle 209 to facilitate the relative movement. (In FIG. 11A, handle 209 is not depicted to the same scale as that of elongated shaft 1104.)

Hollow shaft 1104 may also include a tube (for example, tube 205 of FIG. 2 or tube 705 of FIG. 7), and the cable of wires may be connected to a distal end of the tube (not shown). The cable may include a proximal segment 1102, at least one transition segment 1103, and a distal segment 1105. Proximal segment 1102 may be configured to transfer torque. In some embodiments, for example, a torque device, such as a torquer, may be threaded over the proximal end of the elongated shaft 1104 and tightened over the proximal end of the elongated shaft 1104. A rotational force exerted on the proximal end of the elongated shaft 1104, using the torquer, may cause a rotational force to be applied to a working element located proximate the distal end of the elongated shaft 1104. The ratio of the rotational force exerted on the proximal end of the elongated shaft 1104 to the rotational force applied to the working element may be approximately 1:1. The position of the torquer over the elongated shaft 1104 may be adjusted.

In some embodiments, proximal segment 1102 may be more rigid, compared to at least one transition segment 1103 and distal segment 1105, such that proximal segment 1102 may be configured to transfer torque. Proximal segment 1102 may be formed of a first number of wires, and the first number of wires required to form proximal segment 1102 may be based on certain constraints. For example, certain constraints may include an outer diameter of the cable, an inner diameter of the cable, or an optimal cable angle for torque transfer. In some embodiments, proximal segment 1102 may be formed of about 5-20 wires. For example, proximal segment 1102 may be formed of about 9 wires. In another example, proximal segment 1102 may be formed of about 10 wires.

The cable may further include at least one transition segment 1103 adjacent to the proximal segment 1102. Transition segment 1103 may be configured to provide a gradual transition between the proximal segment 1102 and a distal segment 1105. In some embodiments, the cable may include about 1-10 transition segments 1103. For example, the cable may include about 2 transition segments 1103. The number of transition segments 1103 may vary based on various parameters, including rigidity of proximal segment 1102, flexibility of distal segment 1105, length of the elongated shaft 1104, a length of the cable, or number of wires used to form the cable. Transition segment 1103 may be formed of about 2-19 wires. For example, transition segment 1103 may be formed of about 3-6 wires. If the cable includes more than one transition segment 1103, the number of wires used to form each transition segment 1103 may vary. For example, the number of wires used to form each transition segment may decrease as transition segment 1103 moves closer to distal segment 1105, to thereby provide gradual increase in flexibility from proximal segment 1102 to distal segment 1105.

Distal segment 1105 may be configured to be atraumatic, and thus, may be configured to be very flexible. Accordingly, distal segment 1105 may be more flexible than proximal segment 1102 and at least one transition segment 1103. In order to maintain flexibility, distal segment 1105 may be formed of about 1-5 wires. For example, distal segment 1105 may be formed of about 1-2 wires, and thus, may enable small coil winding, which may determine the flexibility of distal segment 1105.

While proximal segment 1102, transition segment 1103, and distal segment 1105 appear to have a constant cable diameter in FIG. 11A, the segments may not necessarily have a constant diameter. For example, the diameter of transition segment 1103 may be smaller than the diameter of proximal segment 1102, and the diameter of distal segment 1105 may be smaller than the diameter of the transition segment 1103. By way of example, the diameter of hollow shaft 1104 may gradually decrease from proximal segment 1102 to distal segment 1105. Accordingly, coil winding may decrease from proximal segment 1102 to distal segment 1105, to thereby achieve rigidity at proximal segment 1102, relative to distal segment 1105, and flexibility at distal segment 1105, relative to proximal segment 1102. Rigidity may gradually decrease from proximal segment 1102 to distal segment 1105.

Figure 11B:
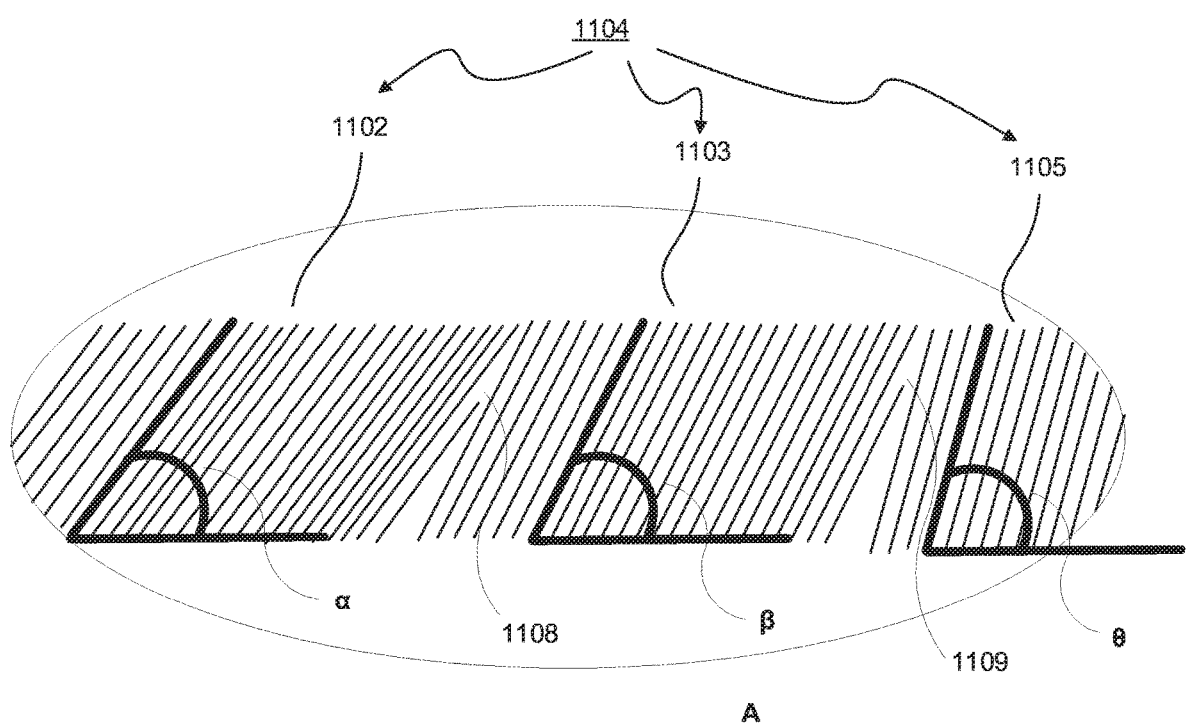
FIG. 11B is an illustration of a section of the exemplary endovascular device of FIG. 11A, consistent with at least one of the disclosed embodiments.

FIG. 11B illustrates section A of exemplary endovascular device 1101 of FIG. 11A, in accordance with the disclosure. In addition to decreasing the number of wires, the pitch angle at which the wires are wound may vary from proximal segment 1102 to distal segment 1105, to thereby transfer maximum torque while maintaining tip flexibility and structural strength of endovascular device 1101. As seen in FIG. 11B, proximal segment 1102 may be formed of a first number of wires wound at a first pitch angle $\alpha$. In addition, at least one transition segment 1103 may be formed of a second number of wires (less than the first number of wires) wound at a second pitch angle $\beta$. Finally, distal segment 1105 may be formed of a third number of wires (less than the second number of wires) wound at a third pitch angle $\theta$. As illustrated in FIG. 11B, the pitch angle may refer to the angle, relative to the bottom planar surface of the hollow shaft 1104, at which the wires are wound. The pitch angle, at which the wires are wound to form the cable, may increase gradually from proximal segment 1102 to distal segment 1105. For example, pitch angle $\alpha$ may be smaller than pitch angle $\beta$, and pitch angle $\beta$ may be smaller than pitch angle $\theta$. Increasing the pitch angle $\theta$ at distal segment 1105 may make distal segment 1105 more bendable. Although FIG. 11B only illustrates one transition segment 1103 formed of wires wound at pitch angle $\beta$, hollow shaft 1104 may include two or more transition segment 1103 at varying pitch angles. For example, hollow shaft 1104 may include a first transition segment and a second transition segment, and the first transition segment may be formed of wires wound at a smaller pitch angle than the wires forming the second transition segment. In some embodiments, hollow shaft 1104 may include at least three transition segments 1103.

In some embodiments, the pitch angle may be determined by various parameters, including, for example, a diameter of a winding mandrel, a diameter of the wire, and a number of wires required to form each segment. By way of example, assuming that the diameter of the wire and the initial cable diameter are known, then the diameter of the winding mandrel and the number of wires required may be calculated to obtain the optimal pitch angle. As such, the diameter of the winding mandrel may be increased or decreased to compensate for any changes in the pitch angle.

In order to provide a gradual transition in flexibility by decreasing the number of wires used from proximal segment 1102 and ultimately to distal segment 1105, the wires may need to be cut. By way of example, at a distal end 1108 of proximal segment 1102, one or more wires used to form proximal segment 1102 may be cut or removed during the winding process. Then, the remaining wires used to form proximal segment 1102 may be used to continue winding and forming transition segment 1103. Likewise, at a distal end 1109 of transition segment 1103, one or more wires used to form transition segment 1103 may be cut or removed during the winding process. Then, the remaining wires used to form proximal segment 1102 and transition segment 1103 may be used to continue winding and forming distal segment 1105. If hollow shaft 1104 includes two or more transition segments 1103, the process may be repeated by removing more wires and continuing to wind the remaining wires to form another transition segment 1103. As such, at least one common wire may be continuously wound to form proximal segment 1102, at least one transition segment 1103, and distal segment 1105. Therefore, instead of forming separate segments and connecting the segments together, the entire cable with proximal segment 1102, at least one transition segment 1103, and distal segment 1105 can be made with the same wire. By providing a continuous, gradual cable without any connection points along the cable, this obviates the need to incorporate rigid connections to connect separate segments together, thereby improving the flexibility of the cable.

Figure 11C:
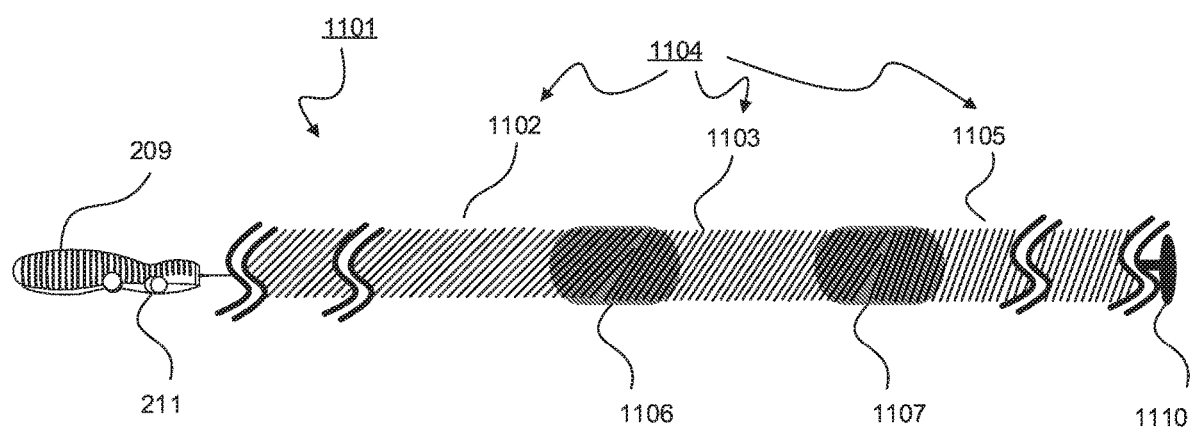
FIG. 11C is an illustration of the exemplary endovascular device of FIG. 11A, consistent with at least one of the disclosed embodiments.

Once wires are cut during the winding process, exposed edges of the cut wires may be dangerous, particularly when endovascular device 1102 needs to be inserted inside the blood vessel. Therefore, as seen in FIG. 11C, once the winding process is finished, the cable may be post-processed by cutting any excess wires and covering the exposed edges of the cut wires with a material 1106. By way of example, material 1106 used to cover exposed edges of the cut wires may include any adhesives, epoxy glues, heat shrink, polyether ether ketone (PEEK), or any other bonding material.

In some embodiments, after wires are cut or removed during the winding process, the pitch angle at which the wires are wound may also change as a result, and thereby reduce the optimal torque transmission of the cable. Accordingly, a diameter of the winding mandrel may need to be adjusted in order to compensate for the wire removal. By way of example, at the distal end 1108 of proximal segment 1102 or at the distal end 1109 of transition segment 1103, one or more wires may be cut or removed. Therefore, at the distal end 1108 of proximal segment 1102 or at the distal end 1109 of transition segment 1103, the diameter of the winding mandrel may be decreased in order to compensate for the reduction in the number of wires used to form each segment. By decreasing the diameter of the winding mandrel, the pitch angle, at which the wires are wound to form each segment, may remain optimal without any overlapping of wires. For example, by decreasing the diameter of the winding mandrel, the pitch angle may remain constant without any overlapping of the wires. The diameter of the winding mandrel may be determined based on the number of wires used, the diameter of the wires, and the required pitch angle at each segment.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods can be modified in any manner, including by reordering steps or inserting or deleting steps. It is intended, therefore, that the specification and examples be considered as example only, with a true scope and spirit being indicated by the following claims and their full scope of equivalents.

What is claimed is:

1. A method of manufacturing an endovascular device, the method including:
   forming a hollow shaft sized for insertion into a blood vessel, the hollow shaft having a proximal end and a distal end;
   disposing a control line having a proximal end and a distal end through the hollow shaft;
   deforming the control line such that the control line has a non-round cross-section, thereby preventing axial rotation between the control line and the hollow shaft; and
   connecting an actuator at the proximal end of the control line, wherein the actuator is configured to exert the actuation force on the proximal end of the control line and cause relative movement between the control line and the hollow shaft, wherein forming the hollow shaft includes:
      winding a plurality of wires on a winding mandrel at a first pitch angle to form a proximal segment of a cable;
      cutting a first subset of the plurality of wires forming the proximal segment, with a first remainder of the plurality of wires remaining;
      winding the first remainder of the plurality of wires on the winding mandrel at a second pitch angle to form a transition segment of the cable;
      cutting a second subset of the first remainder of the plurality of wires forming the transition segment, with a second remainder of the plurality of wires remaining; and
      winding the second remainder of the plurality of wires on the winding mandrel at a third pitch angle to form a distal segment of the cable,
   wherein a diameter of the winding mandrel is changed to compensate for a reduction in a number of the plurality of wires, and
   wherein a change in the diameter of the winding mandrel is determined based on the number of the plurality of wires, a diameter of the plurality of wires, and a pitch at each segment of the cable.

2. The method of claim 1, further including changing the diameter of the winding mandrel after winding the plurality of wires at the first pitch angle and before winding the first remainder of the plurality of wires at the second pitch angle, to thereby compensate for a change in pitch angle.

3. The method of claim 1, further including changing the diameter of the winding mandrel after winding the first remainder of the plurality of wires at the second pitch angle and before winding the second remainder of the plurality of wires at the third pitch angle, to thereby compensate for a change in pitch angle.

4. A method of manufacturing an endovascular device, the method including:
   forming a hollow shaft sized for insertion into a blood vessel, the hollow shaft having a proximal end and a distal end;
   disposing a control line having a proximal end and a distal end through the hollow shaft;
   deforming the control line such that the control line has a non-round cross-section, thereby preventing axial rotation between the control line and the hollow shaft; and
   connecting an actuator at the proximal end of the control line, wherein the actuator is configured to exert the actuation force on the proximal end of the control line and cause relative movement between the control line and the hollow shaft, wherein forming the hollow shaft includes:
      winding a plurality of wires on a winding mandrel at a pitch angle to form a proximal segment of a cable;
      cutting a first subset of the plurality of wires forming the proximal segment, with a first remainder of the plurality of wires remaining;
      decreasing a diameter of the winding mandrel;
      winding the first remainder of the plurality of wires on the winding mandrel at the pitch angle to form a transition segment of the cable;
      cutting a second subset of the first remainder of the plurality of wires forming the transition segment, with a second remainder of the plurality of wires remaining;
      decreasing the diameter of the winding mandrel; and
      winding the second remainder of the plurality of wires on the winding mandrel at the pitch angle to form a distal segment of the cable,
   wherein a change in the diameter of the winding mandrel is determined based on a number of the plurality of wires, a diameter of the plurality of wires, and a pitch at each segment of the cable.

5. The method of claim 1, further including covering exposed edges of the plurality of wires after cutting with a material.

6. The method of claim 5, wherein the material includes at least one of an adhesive, an epoxy glue, a heat shrink, or polyether ether ketone (PEEK).

7. The method of claim 1, further including inserting a material through the hollow shaft to create a non-round cross-section that overlaps with the non-round cross-section of the control line.

8. The method of claim 7, wherein the material includes a rectangular shaped polymer.

9. The method of claim 7, wherein inserting the material through the hollow shaft further includes:
   heating and inserting the material through holes in a wall of the hollow shaft; and
   shaping the material by a rectangular mandrel.

* * * * *